United States Patent [19]

Dietrich

[11] 4,022,879
[45] May 10, 1977

[54] ORAL HYGIENE PRODUCT FOR ANIMALS
[75] Inventor: Ursula Dietrich, San Mateo, Calif.
[73] Assignee: Deepen Enterprises, Inc., San Mateo, Calif.
[22] Filed: Dec. 19, 1973
[21] Appl. No.: 426,151
[52] U.S. Cl. .............................................. 424/49
[51] Int. Cl.$^2$ ........................................ A61K 7/16
[58] Field of Search .............................. 424/49–59

[56] References Cited
UNITED STATES PATENTS 3,087,857  4/1963  Davis et al. ........................... 424/57
3,808,340  4/1974  Palmer ................................ 426/805

OTHER PUBLICATIONS

Stephenson et al.–Veterinary Drug Encyclopedia–12th edition (1964) p. 196.

Primary Examiner—Sam Rosen
Attorney, Agent, or Firm—Townsend and Townsend

[57] ABSTRACT

Method and composition are provided for the care of teeth and the reduction of dental treatment for carnivorous pets, particularly canines. A mildly abrasive, substantially neutral or mildly basic, meat flavored, particularly beef flavored, dentrifice is employed. The dentrifice is found to be acceptable to the animal, causes no harmful effects on ingestion, and greatly reduces the need of a veterinarian's scaling of the pet's teeth.

3 Claims, No Drawings

ORAL HYGIENE PRODUCT FOR ANIMALS

BACKGROUND OF THE INVENTION

1. Field of the Invention

While pets' teeth do not require the same considerations as human teeth, substantial debris is accumulated and tartar formed which can lead to periodontal disease, resulting in bad breath and loss of teeth. Therefore, on a periodic basis, it has been necessary to have veterinarians scale the teeth, so as to remove plaque and tartar which can lead to caries formation, diseases of the gums, or other oral problems. Scaling of a pet's teeth is a time consuming operation which is uncomfortable to the pet. Furthermore, since semi-soft diets are the prevailing diet, substantial tartar and plaque rapidly accumulates creating an offensive breath for the pet which subsists for extended periods of time. With increasing age of the pet, there is increasing concern with diseases of the gums.

In view of the problems with a pet's teeth, it is desirable to find some way to protect the teeth between the extended periods, where the pet is taken to the veterinarian for scaling. However, brushing of a pet's teeth has problems uniquely different from the brushing of a human's teeth. There is the obvious problem of cooperation by the pet as a strange device, such as a toothbrush, is placed in its mouth. Even assuming a docile pet, unlike human beings, the pet will ingest substantially all of the toothpaste, so that the toothpaste must not only be ingestible, but one that does not have undesirable side effects. There is, therefore, a need for a simple and efficient method for brushing a pet's teeth, where any adverse response to the use of a toothbrush is overcome by the desirable or pleasant experience produced by the toothpaste or powder.

2. DESCRIPTION OF THE PRIOR ART

Conventional toothpaste compositions may be found in U.S. Pat. Nos. 2,839,448; 2,876,166; 2,946,725 and 3,227,618.

SUMMARY OF THE INVENTION

Method and composition are provided for cleaning a carnivorous pet's teeth, particularly canines, whereby a mildly neutral or basic stable toothpaste composition is employed having a mild abrasive, which is a mixture of two ingestible abrasives, and flavored with a meat flavor, particularly a beef flavor. It is found that the flavoring agent overcomes the adverse response to the brushing of animals' teeth, particularly canines, so that the pet does respond in a positive and cooperative way to the dental hygienic treatment.

DESCRIPTION OF THE SPECIFIC EMBODIMENTS

A method is provided employing a novel toothpaste composition for oral hygiene for carnivorous pets. The toothpaste composition is a stable ingestible composition having a mixture of mild abrasives, a desirable consistency, and flavored with an attractive meat flavoring, particularly beef flavoring. The toothpaste is employed in a normal manner employing a toothbrush, and the teeth of the pet brushed in substantial conformance with the manner employed for brushing one's own teeth.

The major ingredient of the toothpaste is the abrasive composition. Employed in the abrasive composition is a physiologically acceptable form of kaolin, which is a hydrated aluminum silicate, and calcium carbonate. The amount of the abrasive will be greater than about 50 weight % of the total composition and usually less than about 80 weight %, generally ranging from about 60 to 75 weight %. The amount of calcium carbonate will not exceed 60 weight % of the abrasive portion of the composition and will be at least about 30 weight %, generally being in the range of about 40 to 55 weight %, and particularly preferred, 50%. As for the total composition, the calcium carbonate will generally be in the range of about 20 to 40 weight %. Since the calcium carbonate is the more abrasive of the two materials, the amount employed should be sufficient to provide the desired abrasive quality to the toothpaste, but not so great as to cause any deterioration of the enamel.

The other material employed as an abrasive will be kaolin, which will be present in amounts of from about 40 to 70 weight % of the abrasive composition, more usually in amounts of about 45 to 60 weight % of the abrasive composition. As for the total composition, the amount of kaolin will generally be in the range of about 25 to 45 weight %, more usually from about 30 to 40 weight %.

Normally, at least about 0.5 weight % and not more than about 2 weight %, more usually from about 0.8 to 1.2 weight % and preferably about 1 weight % of aluminum hydroxide will be added. The aluminum hydroxide insures that there be a substantially neutral or mildly basic pH to the paste.

A small but sufficient amount of a physiologically acceptable humectant will also be employed, normally being used in amounts of from about 5 to 20 weight %, more usually from about 6 to 15 weight %.

The flavoring agent employed will be a meat flavor, particularly beef flavor. Various beef flavors may be employed, both artificial and naturally derived. Illustrative beef flavors include Kuhnstamm, imitation beef flavor P-1420 and Norda imitation beef flavor. It is found that it is usually desirable to also add a small amount of salt, the amount of salt will, however, depend upon the particular beef flavoring employed. Usually, the flavoring agent will be present in from at least about 0.5 weight % and not exceeding 1.5 weight %, preferably being about 1 weight %. The amount of salt will generally be at least about 0.5 weight % and not exceeding 3 weight %, generally being from about 1 to 2 weight %.

Water is then employed to provide the desired consistency and fluidity of the composition. The amount of water will bring the total composition to 100 weight %. Generally, it is found satisfactory to use from about 8 to 25 weight % water, more usually from about 10 to 25 weight % water. The total amount of fluid should not exceed 40 weight %, generally not exceed 35 weight %, and will usually be in the range of about 25 to 30 weight % of the total composition.

An exemplary composition was prepared by combining 30g kaolin, 30g calcium carbonate, 1g aluninum hydroxide USP, 10–15ml water, 6ml glycerin, 1g of Kuhnstamm imitation beef flavor P-1420, and 2g salt.

An oral hygiene program was established employing the above exemplary toothpaste with dogs. It was found that the dogs were cooperative when their teeth were brushed, allowing for an efficient oral hygiene program to protect the dogs' teeth. Ingestion of the toothpaste had no deleterious effect on the dogs' health and seemed to enhance the cooperative response of the dogs.

In accordance with the subject invention, a method of oral hygiene is provided for carnivorous pets, particularly dogs, whereby a stable ingestible meat flavored toothpaste is employed. The pet cooperates with the oral hygiene program, so that the teeth are protected and freed of plaque and tartar to a substantial degree, during the interim period of treatment by a veterinarian.

What is claimed is:

1. A toothpaste composition useful for brushing of carnivorous pets' teeth consisting essentially of a physiologically acceptable mildly abrasive composition, comprising a mixture of kaolin and calcium carbonate, a humectant, a small but sufficient amount of aluminum hydroxide to provide a neutral or mildly basic pH, water, and a small but sufficient amount of a meat flavoring agent.

2. A composition according to claim 1, wherein said mildly abrasive composition is present in from 50 to 80 weight % and is comprised of 30–60 weight % calcium carbonate and 40 to 70 weight % kaolin, said humectant is present in from 5–20 weight % and is glycerine, said water is present in from 8 to 25 weight %, and said meat flavoring is a beef flavor.

3. A composition according to claim 2, wherein said mildy abrasive composition is present in from 60–75 weight % and is comprised of 40–55 weight % calcium carbonate and 45–60 weight % kaolin, said humectant is present in from 6–15 weight % and is glycerine, and said composition contains water in from 10–25 weight %.

* * * * *